(12) United States Patent
Weldon et al.

(10) Patent No.: US 8,221,821 B1
(45) Date of Patent: Jul. 17, 2012

(54) METHODS OF MODIFYING ABLUMENAL/LUMENAL STENT COATING THICKNESSES

(75) Inventors: Lisa Weldon, Mountain View, CA (US); Stephen Pacetti, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1245 days.

(21) Appl. No.: 11/983,663

(22) Filed: Nov. 9, 2007

(51) Int. Cl.
*A61F 2/06* (2006.01)
*A61L 33/00* (2006.01)
*B05D 3/12* (2006.01)

(52) U.S. Cl. ...... 427/2.24; 427/2.1; 427/2.25; 623/1.15; 623/1.42; 623/1.44

(58) Field of Classification Search ............ 427/2.1, 427/2.24, 2.25; 623/1.1, 1.15, 1.42–1.44
See application file for complete search history.

(56) References Cited

U.S. PATENT DOCUMENTS

| | | | | |
|---|---|---|---|---|
| 5,575,818 | A | * 11/1996 | Pinchuk | 623/1.15 |
| 5,897,911 | A | 4/1999 | Loeffler | |
| 6,153,252 | A | * 11/2000 | Hossainy et al. | 427/2.3 |
| 6,344,055 | B1 | * 2/2002 | Shukov | 623/1.15 |
| 6,887,510 | B2 | * 5/2005 | Villareal | 427/2.24 |
| 7,201,940 | B1 | 4/2007 | Kramer | |
| 7,485,333 | B2 | 2/2009 | Pacetti et al. | |
| 2004/0208985 | A1 | * 10/2004 | Rowan et al. | 427/2.25 |
| 2006/0036308 | A1 | * 2/2006 | Goshgarian | 623/1.11 |
| 2006/0149365 | A1 | * 7/2006 | Fifer et al. | 623/1.46 |

* cited by examiner

*Primary Examiner* — Timothy Meeks
*Assistant Examiner* — Cachet Sellman
(74) *Attorney, Agent, or Firm* — Squire Sanders (US) LLP

(57) ABSTRACT

The present invention provides a method of manufacturing a stent having a coating, comprising providing a tubular stent having a lumenal side and an ablumenal side; applying a coating composition to the stents such that the coating composition contacts the lumenal and ablumenal sides of the stent; and modifying the diameter of the stent from a first diameter to a second diameter during the process of applying the coating composition.

28 Claims, 3 Drawing Sheets

METHODS OF MODIFYING ABLUMENAL/LUMENAL STENT COATING THICKNESSES

BACKGROUND

1. The Field of the Invention

The present invention relates to drug delivery or drug eluting stents. More specifically, the invention relates to methods for producing drug delivery stent coatings which have variable stent coating thicknesses by changing the stent diameter during the application of the coating process, deposition, or formation.

2. Related Background

Stents are frequently used in the health care industry to open vessels affected by occasions such as stenosis, thrombosis, restenosis, vulnerable plaque, and formation of intimal flaps or torn arterial linings caused by percutaneous translumenal coronary angioplasty (PCTA). Stents are used not only as a mechanical intervention, but also as vehicles for providing biological therapy. As a mechanical intervention, stents act as scaffoldings, functioning to physically hold open and, if desired, to expand the passageway wall. Stents may be capable of being compressed, so that they can be inserted through small cavities via catheters or balloon-catheters and then expanded to a larger diameter once they have been isolated at the target location. There are many examples in the patent literature disclosing stent structures which have been successfully applied in procedures including stents illustrated in U.S. Pat. Nos. 4,733,665 issued to Palmaz, 4,800,822 issued to Gianturco, and 4,886,062 issued to Wikor.

One example of a stent, which is designed to expand and contract under radial pressure is illustrated by FIG. 1. Stent 10 is shown to have struts 12 separated by spaces which allow the stent to be crimped on a catheter or balloon and to allow the stent to follow a tortuous pathway of anatomical structures. In lieu of struts, stents can be made from filaments, fibers, rolled up metal sheets, and a multitude of other mechanical designs with unique geometries which can be found in the medical and patent literature.

In addition to mechanical intervention, stents can be modified by medication to provide for local administration of drugs, bioactive agents, or therapeutic substances, terms which are used interchangeably unless otherwise specifically indicated. Medicated stents provide for the local administration of a therapeutic substance at the diseased site or periphery of the site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

The current standard of coating stents includes the use of a polymer matrix coated onto the surface of a stent. Polymer coated stents have been well enabled and described by the patent literature as of the filing date this invention and for the sake of brevity, no prolonged discussion should be merited for those skilled in the art. Briefly, to a stent is applied a polymer dissolved in a solvent with a drug added thereto. Once the solvent evaporates, a polymer film is left behind with the drug embedded or contained therein. In vivo, the drug releases or elutes out from the polymer.

Although drug delivery stents have shown unmatched advances, as with any invention, room for improvement and modifying weaknesses always exists. Perfecting drug delivery stents can be in the type of polymer or drug used, dosages, advances in coating constructs that tailor specific needs of patient care, fine-tuning of the coating topography that can address specific biological deficiencies. For example, thrombosis can be one adverse clinical sequela of stenting. Some drug eluting stents can have higher incidents of late thrombosis compared to bare metal stents. Even though thrombosis is rare, the consequences of late thrombosis are driving some cardiologist to prescribe prolonged, or even permanent, anti-platelet drug therapy. One concern is whether drug eluting stents re-endothelialize more slowly than bare metal stents. Some cell culture and animal study data suggest that some drugs may counter or inhibit endothelial cell proliferation. This effect appears pronounced nearest the surfaces of the struts, where the drug amount concentration is highest and most prolonged. This effect is of most concern on the lumenal surfaces of the stent struts, where the goal is to have rapid and complete reendothelialization after stent placement.

In some circumstances, there may be a need to have a greater amount or concentration of the drug on the ablumenal surface for better management of restenosis, such that only a small amount of the drug is washed down-stream from the luminal coating by the flow of blood. As yet another coating construct alternative, for certain patient sub-set, it may be beneficial to have a higher anti-restenotic concentration of the drug on the ablumenal surface than the lumenal side and higher concentration of a secondary drug, such as anti-clotting agent (e.g., heparin) or growth factor (e.g., angiogenesis drug, VEGF, etc.), on the lumenal side than the ablumenal side for synergistic effects.

Such ability to modify stent coating can lead to better and effective patient management. The methods of the present invention provide apparatus, means and techniques for achieving these as well as other goals that are apparent to one skilled in the art.

SUMMARY OF THE INVENTION

In accordance with one aspect of the invention, a method of manufacturing a stent having a coating is provided, comprising:

(a) providing a tubular stent having a lumenal (inner) side and an ablumenal (outer or tissue contacting surface) side;

(b) applying a coating composition to the stent such that the coating composition contacts the lumenal and ablumenal sides of the stent; and (c) modifying the diameter of the stent from a first diameter to a second diameter during the process of applying the coating composition. In some embodiments, the modification can cause the thickness of coating manufactured on the ablumenal side of the stent to be 25% to 400% greater than the thickness of coating manufactured in the lumenal side of the stent. Alternatively, in certain circumstances, the modification causes the thickness of coating manufactured on the ablumenal side of the stent to be 25% to 100% less than the thickness of coating manufactured on the lumenal side of the stent. In some embodiments, the method can additionally include applying a second coating composition to the stent such that the second coating composition is applied only subsequent to or only during the modification of the first diameter to the second diameter. The first and second coating compositions can include one or combination of polymer(s), solvent(s), drug(s), biobeneficial agent(s). Any one these components as applied to the first or second coating composition can be the same or different in type, property, composition, or amount. In one embodiment, the method of modifying comprises reducing the diameter of the stent. The modifying comprises decreasing the diameter of the stent by 3% to 97%. In some embodiments, the modifying comprises reducing the diameter of the stent from a range selected from a group of 10% to 90%, 20% to 80%, 30% to 70% and 40% to 60%. In some embodiments, the modification in diameter has to be sufficient to achieve the objectives of the present invention, including providing a discernable difference, for example, in coating thickness, topography or amount or concentration of drug that is placed on lumenal versus ablumenal sides of the stent.

In some embodiments, the modifying comprises increasing the diameter of the stent. The modifying comprises increasing the diameter of the stent by 3% to 97%. In some embodiments the modifying comprises increasing the diameter of the stent from a range selected from a group of 10% to 90%, 20% to 80%, 30% to 70% and 40% to 60%.

In some embodiments, the application of the coating composition is completely terminated before or while the diameter of the stent is modified and then the application of the coating composition or a different coating composition is resumed afterwards.

In some embodiments, the coating composition is continuously applied while the diameter of the stent is modified such that application of the composition is not disrupted.

In some embodiments, the application of the composition can be by a spray technique (e.g., atomized spray methods, vapor deposition, and the like) and wherein the spray is continuously applied while the diameter of the stent is modified such that application of the composition is not disrupted.

In some embodiments, the application of the composition is by a spray technique (e.g., atomized spray methods, vapor deposition, and the like) and wherein stent is rotated about a longitudinal axis of the stent. Rotation can be at any rate, for example from 1 rpm to several hundred rpms depending on the stent, process techniques and materials used.

In accordance to another aspect of the invention, a method of manufacturing a stent having a coating is provided, comprising:

(a) applying a coating composition to the stent positioned at a first diameter on a stent support structure such that the coating composition contacts the lumenal and ablumenal sides of the stent;

(b) modifying the diameter of the stent from the first diameter to a second diameter;

(c) applying a second coating composition to the stent having the second diameter to manufacture a stent coating.

In some embodiments, the modification comprises decreasing the diameter of the stent such that an ablumenal surface of the stent receives a greater amount of the second coating.

In some embodiments, the modification comprises increasing the diameter of the stent such that an ablumenal surface of the stent may receive a lesser amount of the second coating composition.

In some embodiments, the acts of the above described method (a), (b) and (c) are done in sequential order, such that each of (a), (b) and (c) is fully terminated or discontinued prior to the start of the next act.

In some embodiments acts (a), (b) and (c) are performed continuously without any disruption in application of the first coating composition and modification of the diameter of the stent and the modification of the diameter of the stent and the application of the second coating composition.

In some embodiments acts (a) and (b) at least in part overlap, followed by termination of act (a) and/or (b), followed by act (c).

In some embodiments act (a) is first performed, then terminated, followed by (b) and (c) which could at least in part be overlapping acts.

In some embodiments, the diameter of the stent is modified during a period of application of the first and/or second coating compositions.

In some embodiments, the diameter the stent is held constant during at least a period of application of the first and/or second coating compositions.

The coating compositions can be for primer layers, pure drug layers, pure polymer layers, polymer/drug layers, topcoat layers, bioactive finishing coat layers and one or more layers can be used in combination with another type of layer. The methods also include using the same or using different polymer(s), drug(s), polymer: drug ratio, etc. for each layer constructed.

DETAIL DESCRIPTION

Figure 1:
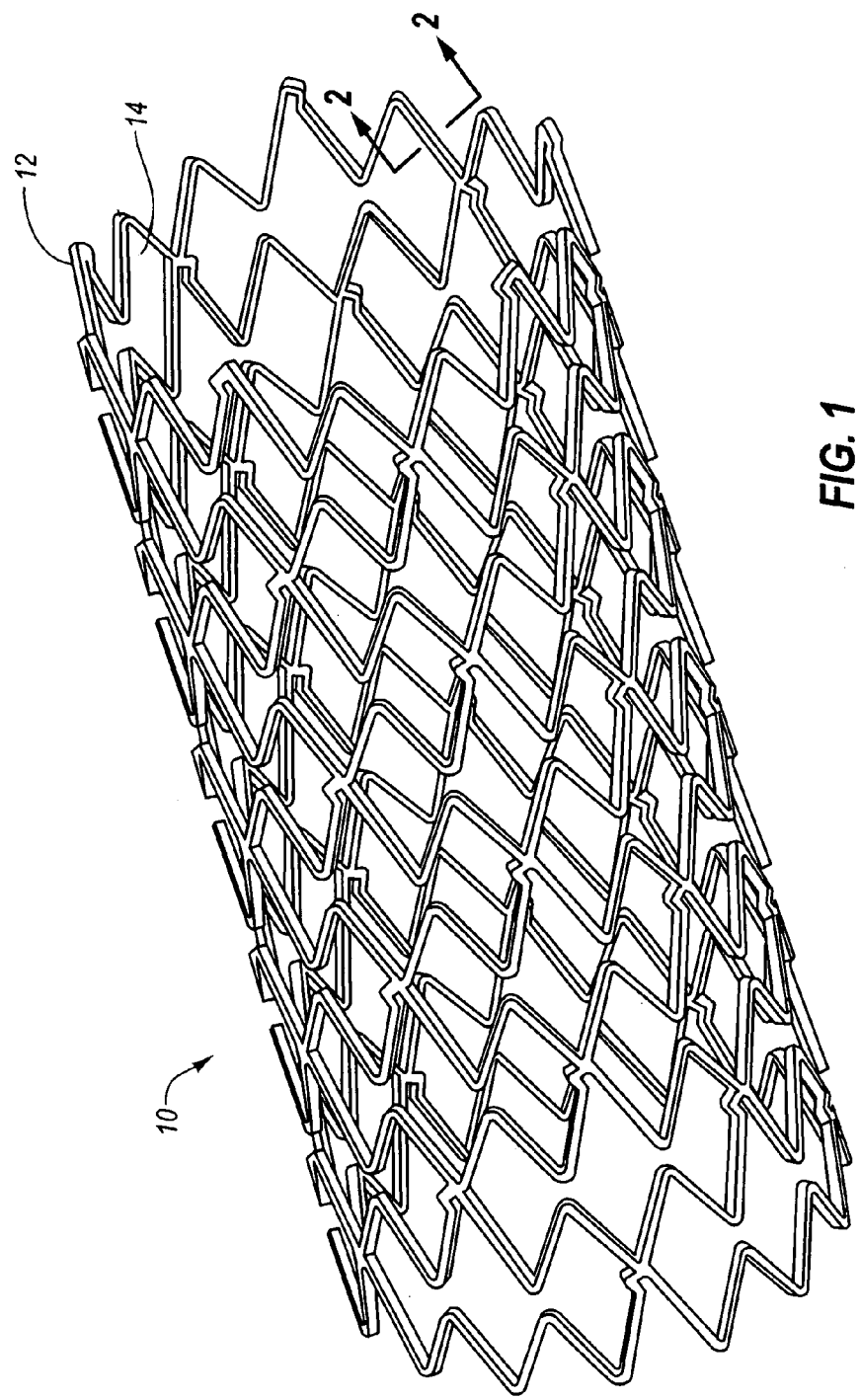
FIG. 1 is an illustration of a conventional stent that can be made from a metal or polymer and can be coated with a drug delivery matrix. The stent can be catheter-balloon expandable or self-expandable, for example. The stent is shown as having struts or patterned frame separated by gaps or spaces which would allow for fluid flow or growth of biological tissues.

FIG. 1 illustrates a conventional stent 10 that can be made from a metal, polymer or combination of metal and polymer and can be coated with a drug delivery matrix. The stent can be catheter-balloon expandable or self-expandable, for example. The stent is shown as having struts or patterned frame 12 separated by gaps or spaces 14 which would allow for fluid flow or growth of biological tissues. In some embodiments, stents are distinguished from grafts and stent-grafts which are considered in the art to be very different types of medical devices with different applications. Stent are also not related to simple tubular devices that are not intended to perform a function of a stent, which would include, for example, maintaining vascular patency, drug delivery and the like. Stents are sized so that they can be delivered, for example, percutaneously and expanded at the target site in need of mechanical or biological therapy for a patient. The pattern of the struts and the material from which the struts are made can dictate the stent's functionality, such as how the stent can expand, lock into position, and be crimped on a balloon of a catheter or inserted into a sheath for delivery. The frame pattern, the material and how the stent is made can also dictate how flexible the stent is radially and longitudinally and how much the stent can twist around its body, which can be critical when there is a need to traverse overly tortuous biological passageways. Stent are not just used for an arterial or venous vasculature, as they can also be used in other bodily lumens and cavities such as the urethra, ureter, fallopian tubes, esophagus, and the like. Preferably, the stent is a vascular stent.

With the embodiments of the invention, the stent can be coated with one or any combination of the following layers: primer layer (e.g., of a polymer), pure polymer layer, adhesive or bio-adhesive layer (e.g., sugar), pure drug layer (e.g., everolimus), polymer drug layer, top-coat layer (e.g., of a polymer), or biobeneficial layer or a finishing coat layer (e.g., polyethylene glycol, heparin, etc.). For example, in one embodiment, the stent can include a primer layer covered by a drug polymer layer. As another example, the stent can include a first drug polymer layer beneath a second drug polymer layer. As another example, a stent can include a primer layer, a drug polymer layer, and a top-coat layer of pure polymer to control the release of the drug. For each of the layers, if multiple layers are used, the type or property of the material (e.g., polymer or drug) can be different. For each of the layers, if multiple layers are used, the ratio of the components used can be the same or different. For example, if multiple drug polymer layers are deposited, the ratio of the drug to polymer in the first layer can be different than in the second layer as well as the type of drugs and polymers used in each layer can be different.

The stent can be coated by a variety of techniques, including spraying, sputtering, evaporation methods, atomized spraying, dipping, vapor deposition, electrospraying, electrostatic deposition, etc. Any suitable fluid or vapor droplet technique as is known to those skilled in the art can be used with the methods of the present invention. Preferably, the method of coating includes spraying via an internal or external atomizing nozzle assembly that projects small droplets of a coating composition onto the ablumenal (outer or tissue or vessel contacting) and lumenal (inner) surfaces of the stent. The small droplets project through the gaps 14 of the stent for lumenal side coating applications. The coating composition can be wet, such as with compatible solvents combined with the polymer and drugs and other materials used. The viscosity or wetness of the composition depends on variety of factors including stent geometry, strut material, type of polymer and drug and variables well known to one having skilled in the art. During the coating process or spray application, the stent can be rotated for even distribution of the coating composition. Rotation is preferably about a longitudinal axis symmetrical with the center of the stent so as to provide even composition distribution. Rotation can be from 1 rpm to well over 500 rpm. The stent can be attached to a mounting assembly, such as a mandrel, a chuck, or the like for support and rotation. There are many examples in the patent literature with regards to mounting assembly, and rotation of stent during coating process is well within the familiarity of one skilled in the art.

In one embodiment, a method is provided which includes applying a coating composition to the stent such that the coating composition contacts the lumenal and ablumenal sides of the stent and the diameter of the stent is modified from a first diameter to a second diameter. The first diameter can be less than or greater than the second diameter. This will cause the thickness of the coating manufactured on the ablumenal side to be greater than or less than the thickness of the coating on the lumenal side. When the diameter is decreased or if the frame elements 12 are positioned closer to one another, less of the coating composition can penetrate into the gaps 14, thereby coating the lumenal side of the stent. Accordingly, a thicker coating can be gained on the ablumenal side. Conversely, when the diameter of the stent is increased or the frame elements 12 are distanced or widened from each other, it may be possible that more coating composition can be deposited on the lumenal side of the stent and less coating is capable of being gathered on the ablumenal side. Accordingly, it may be possible that a thinner coating might be gained on the ablumenal side.

Thrombosis is one adverse clinical sequela of stenting. Some drug eluting stents can have higher incidents of late thrombosis compared to bare metal stents. Even though thrombosis is rare, the consequences of late thrombosis are driving some cardiologist to prescribe prolonged, or even permanent, anti-platelet drug therapy. One concern is whether drug eluting stents re-endothelialize more slowly than bare metal stents. Some cell culture and animal study data suggest that the drugs may counter or inhibit endothelial cell proliferation. This effect appears pronounced on the surfaces of the struts, where the drug amount concentration is highest and most prolonged. Of most concern is the presence of high or prolonged concentrations of drug on the lumenal surfaces where reendothelialization may be impaired after stent placement. Accordingly, by the methods of the present invention, lesser concentration, amount, or dose of drug can be placed on lumenal surface or face of the stent struts which can directly and intimately contact the neointimal and regrown endothelial layer.

In some embodiments, there may be a need to have a greater amount or concentration of the drug on the ablumenal surface for better management of restenosis, such that only a small amount of the drug is washed down-stream from the lumenal coating by the flow of blood. As yet another coating construct alternative, for certain patient sub-set, it may be beneficial to have a higher anti-restenotic concentration, amount or dose of the drug on the ablumenal surface and a lower concentration, amount or dose secondary drug, such as anti-clotting (e.g., heparin) or growth factor (e.g., angiogenesis drug, VEGF, etc.) on the lumenal side for synergistic effects.

The methods of the present invention allow for these and a multitude of variety of coating constructs. As yet another example, with the method of the present invention, a thicker topcoat layer can be applied to the ablumenal side as compared to the lumenal side, over a drug reservoir polymer layer. This can cause the release rate of the drug to be slower or longer in duration on the ablumenal side than the lumenal side since the drug has to travel through a thicker ablumenal top coat layer.

Figure 3:
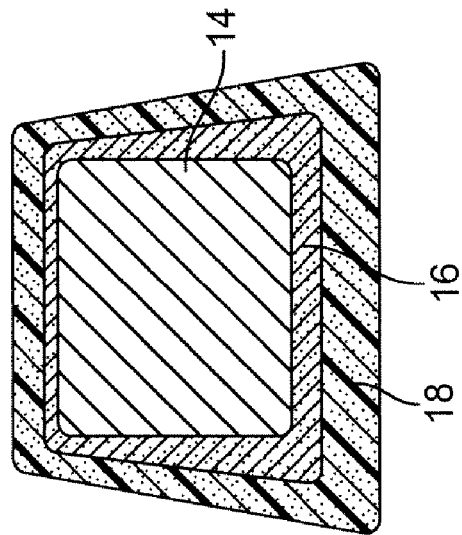
FIG. 3 illustrates one coating construct according to an embodiment of the invention.
Figure 2:
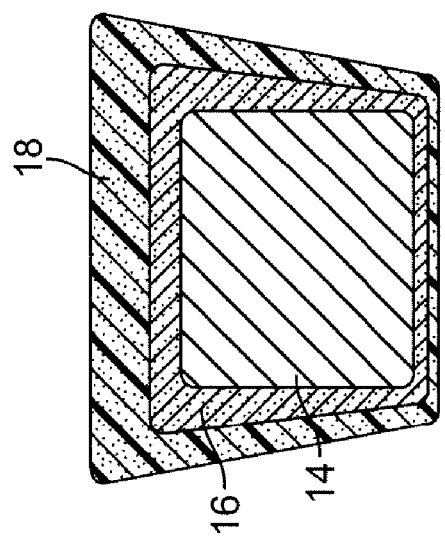
FIG. 2 illustrates one coating construct according to an embodiment of the invention.

Two examples are shown by FIGS. 2 and 3 for illustrative purposes. The cross section of the strut is labeled as 14. In FIG. 2, a first layer or film of conformal uniformity is deposited on the surface of the strut 14, extending around the perimeter of the strut. The first layer 16 can be a primer layer, an adhesive layer such as a bio-adhesive, a pure drug layer, or a polymer-drug layer. A second layer or film 18 is shown being thicker on the ablumenal side than the lumenal side as produced in accordance with a method of the present invention. The second layer 18 can be a pure drug layer, polymer-drug layer, top-coat layer, biobeneficial layer or finishing coat layer.

In FIG. 3 a first layer or film 16 of conformal uniformity is deposited on the surface of the strut 14, extending around the perimeter of the strut. The first layer 16 can be a primer layer, an adhesive layer such as a bio-adhesive, a pure drug layer, or a polymer-drug layer. A second layer or film 18 is shown being thinner on the ablumenal side than the lumenal side as produced in accordance with a method of the present invention. The second layer 18 can be a pure drug layer, polymer-drug layer, top-coat layer, biobeneficial layer or finishing coat layer.

One skilled in the art can certainly appreciate that any number of layers having a variety of configurations can be deposited. For example, embodiments of FIGS. 2 and 3 can be combined to produce a conformal primer layer, a first polymer-drug layer being thicker on the ablumenal side and thinner on the lumenal side and a second polymer-drug layer being thicker on lumenal side than the ablumenal side. In yet another configuration, an optional conformal primer layer can be provided followed by a polymer-drug layer being thicker on the ablumenal side and thinner on the lumenal side and a top-coat layer being thicker on the ablumenal side and thinner on the lumenal side. In yet another confirmation, an optional conformal primer layer can be provided followed by a polymer-drug layer being thicker on the ablumenal side and thinner on the lumenal side and a top-coat layer being thicker on the lumenal side and thinner on the ablumenal side. In yet another configuration, an optional conformal primer layer can be provided followed by a first polymer-drug layer being thicker on the ablumenal side and thinner on the lumenal side and a second polymer-drug layer being thicker on the ablumenal side and thinner on the lumenal side.

The modification of the diameter can cause the thickness of the coating manufactured on the ablumenal side of the stent to be at least 5% greater than the thickness of the coating manufactured on the lumenal side of the stent. In some embodiments, the percentage can be at least 10%, 15%, 20% or 25%. In some embodiments the modification of the diameter can cause the thickness of the coating manufactured on the ablumenal side of the stent to be 5% to 100, 200, 300 or 400% greater than the thickness of the coating manufactured on the lumenal side of the stent.

Alternatively, it may be possible that the modification of the diameter in the opposite direction may cause the thickness of the coating manufactured on the lumenal side of the stent to be at least 5% greater than the thickness of the coating manufactured on the ablumenal side of the stent. In some embodiments, the percentage can be at least 10%, 15%, 20% or 25%. In some embodiments the modification of the diameter can cause the thickness of the coating manufactured on the lumenal side of the stent to be 25% to 100% greater than the thickness of the coating manufactured on the ablumenal side of the stent.

Change to the diameter of the stent during the manufacturing process can be at least 3% to about 97%. Any range therein also falls within the scope of the present invention including 5% to 95%, 10% to 90%, 15% to 85%, 20% to 80%, 25% to 75%, 30% to 70% and 40% to 60%. Again, the modifying can be increasing or decreasing of the diameter of the stent but is at least after some amount of composition is applied to the stent and the invention does not encompass any pre-coating modification such as that which may inherently occur while the stent is being positioned on a support device or any intentional modification that the manufacturer may make to the diameter prior to the initiation of the application of the coating composition.

Again, the modification of the diameter of the stent is after at least some amount of application of the coating composition to the stent. In one embodiment, the application of the coating composition is completely terminated while the diameter of the stent is modified, and the application of the coating composition is then resumed again after the modification of the diameter of the stent.

In some embodiments, the modification of the diameter of the stent can be initiated at the same exact time that the coating composition is applied to the stent and the modification of the diameter can terminate some time before or at the same exact time the application of the coating composition is terminated. In some embodiments, the modification of the diameter of the stent can be initiated at a time subsequent to initiation of the application of the coating composition and can be terminated some time before or at the same exact time the application of the coating composition is terminated. The modification can be at a constant rate from a first diameter to a second diameter or the rate can vary during this change. The modification can be from a first diameter to a second diameter followed by any other number of diameters such that the change can be in incremental, step-wise fashion.

In some embodiments, the coating composition is continuously applied while the diameter of the stent is modified such that application of the composition is not disrupted. As indicated above, preferably, the application of the coating composition is by a spray technique such that the spray is continuously applied while the diameter of the stent is modified and that application of the composition is not disrupted.

In some embodiments, modification of the diameter only occurs when the coating composition is not in any way applied to the stent (e.g., spray process is completely stopped) such that during the spray process the diameter of the stent is held constant with 0% deviation. In some embodiments, the rotation of the stent on the support structure may cause minimal diameter variation but such variation should be considered minimal and within the definition of the diameter being held "constant."

As previously indicated, multiple coating layers can be applied such that each layer can have an even or conformal thickness on the ablumenal and lumenal sides, be thicker on the ablumenal side than the lumenal side or be thinner on the ablumenal side than the lumenal side. Such a method of deposition can include the following steps or acts: (a) applying a coating composition to the stent positioned at a first diameter on a stent support structure such that the coating composition contacts the lumenal and ablumenal sides of the stent; (b) modifying the diameter of the stent from the first diameter to a second diameter; and (c) applying a second coating composition to the stent having the second diameter such that the second coating composition contacts the lumenal and ablumenal sides of the stent. In one embodiment, the modification comprises decreasing the diameter of the stent such that an ablumenal surface of the stent receives a greater amount of the second coating. In an alternative embodiment, the modification comprises increasing the diameter of the stent such that it may be possible that an ablumenal surface of the stent receives a lesser amount of the second coating composition. In some embodiments, the steps or acts (a), (b) and (c) are done in sequential order, such that each of (a), (b) and (c) is fully terminated or discontinued prior to the start of the next step or act. In some embodiments, steps or acts (a), (b) and (c) are performed continuously without any disruption in application of the first coating composition and modification of the diameter of the stent and the modification of the diameter of the stent and the application of the second coating composition. In some embodiments, steps or acts (a) and (b) at least in part overlap, followed by termination of act (a) and/or (b), followed by act (c). In some embodiments, step or act (a) is performed first, then terminated, followed by (b) and (c) at least in part overlapping. Again, as previously mentioned the diameter of the stent can be modified during a period of application of the first and/or second coating compositions. Also, the diameter the stent can be held constant during at least a period of application of the first and/or second coating compositions.

Figure 4A:
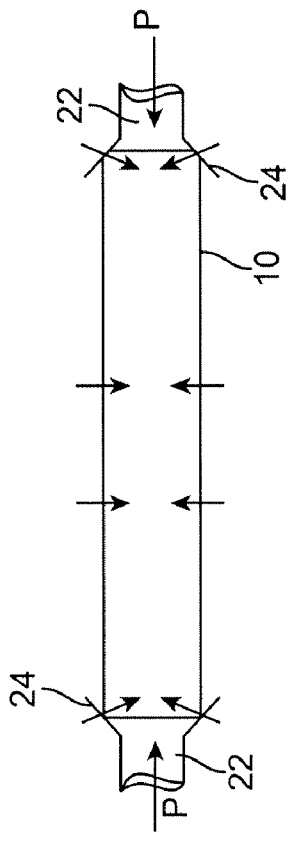
FIGS. 4A-4C illustrate various techniques of embodiments of the present invention to modify the coating constructs.
Figure 4B:
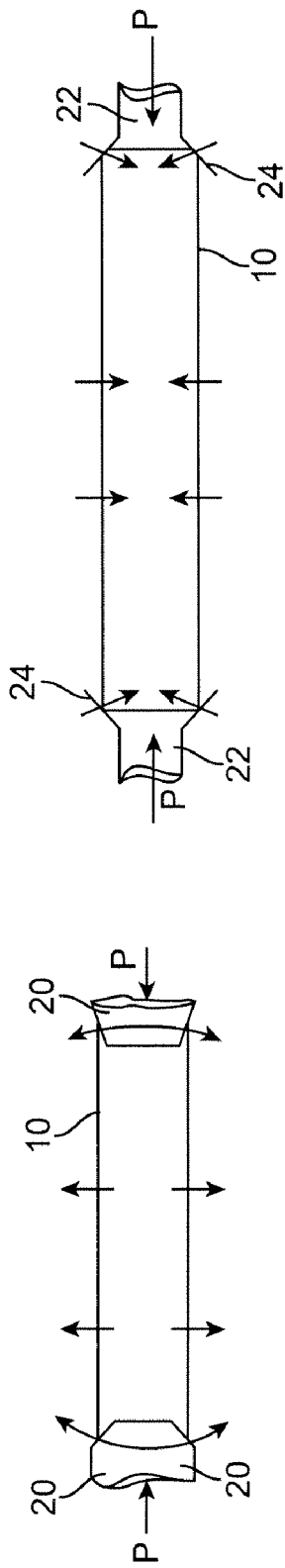
Figure 4C:
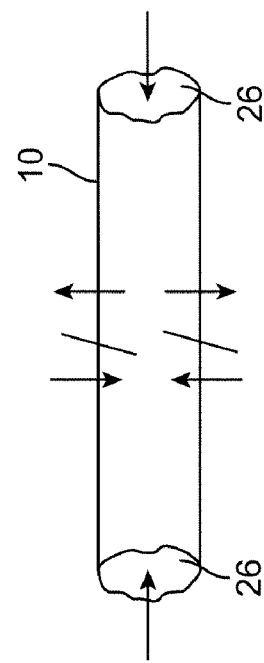

The diameter of the stent can be modified by a variety of devices, technique and means. In one embodiment, as illustrated by FIG. 4A, stent 10 ends are supported by coning elements, bars, or chucks 20 that are at least partially penetrated into the stent ends. Application of pressure P will cause the stent to expand in diameter. FIG. 4B illustrates chucks 22 into which stent 10 ends are positioned. Chuck 22 includes end caps 24 that can resemble concave discs such that when inward pressure P is applied, the discs can apply even and symmetrical radial pressure on the outer stent ends, causing the stent to contract. A means for diameter modification can also include a balloon or inflatable bladder 26 of FIG. 4C which can be hydraulic or pneumatic. It should be noted that the support devices or support means such as elements, bars, chucks, balloons, or bladders should make minimum contact with the stent so that both the ablumenal and lumenal surfaces are accessible for receiving the coating composition. Techniques to reduce the stent diameter can involve the various apparatus used for crimping stents. These include wedge crimpers, iris crimpers, sector crimpers, and crimpers that function by rolling the stents between two flat plates. Unlike crimping operations onto balloon catheters, in this case the diameter is only partially reduced.

In any of the embodiments, the coating composition can include one or a combination of solvent(s), polymer(s) and drug(s). Representative biocompatible polymers include, but are not limited to, poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly (ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl fluoride such as polyvinylidene fluoride (PVDF) or poly(vinylidene fluoride-co-hexafluoropropylene) (PVDF-HFP), poly(tetrafluoroethylene-co-vinylidene fluoride-co-hexafluoropropylene), polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), polypropylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayontriacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(etheresters) (e.g. poly(ethylene oxide/poly(lactic acid) (PEO/PLA)), polyalkylene oxides such as poly(ethylene oxide), polypropylene oxide), poly(ether ester), polyalkylene oxalates, polyphosphazenes, phosphoryl choline, choline, poly(aspirin), polymers and co-polymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly (methyl methacrylate)-PEG (PMMA-PEG), polydimethylsiloxane-co-PEG (PDMS-PEG), PLURONIC™ surfactants (polypropylene oxide-co-polyethylene glycol), poly(tetramethylene glycol), hydroxy functional poly(vinyl pyrrolidone), biomolecules such as chitosan, alginate, fibrin, fibrinogen, cellulose, starch, dextran, dextrin, fragments and derivatives of hyaluronic acid, heparin, fragments and derivatives of heparin, glycosamino glycan (GAG), GAG derivatives, polysaccharide, chitosan, alginate, or combinations thereof. In some embodiments, the copolymer described herein can exclude any one or more of the aforementioned polymers. As used herein, the terms poly(D,L-lactide), poly(L-lactide), poly(D,L-lactide-co-glycolide), and poly(L-lactide-co-glycolide) can be used interchangeably with the terms poly(D,L-lactic acid), poly(L-lactic acid), poly(D,L-lactic acid-co-glycolic acid), or poly(L-lactic acid-co-glycolic acid), respectively.

Examples of drugs, therapeutic agents or bioactive agents include, but are not limited to, synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules that bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. The bioactive agents could be designed, e.g., to inhibit the activity of vascular smooth muscle cells. They could be directed at inhibiting abnormal or inappropriate migration and/or proliferation of smooth muscle cells to inhibit restenosis. In certain embodiments, optionally in combination with one or more other embodiments described herein, the implantable device can include at least one biologically active agent selected from antiproliferative, antineoplastic, antimitotic, anti-inflammatory, antiplatelet, anticoagulant, antifibrin, antithrombin, antibiotic, antiallergic and antioxidant substances. An antiproliferative agent can be a natural proteineous agent such as a cytotoxin or a synthetic molecule. Examples of antiproliferative substances include, but are not limited to, actinomycin D or derivatives and analogs thereof (manufactured by Sigma-Aldrich, or COSMEGEN available from Merck) (synonyms of actinomycin D include dactinomycin, actinomycin IV, actinomycin $I_1$, actinomycin $X_1$, and actinomycin $C_1$); all taxoids such as taxols, docetaxel, and paclitaxel and derivatives thereof; all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Examples of rapamycin derivatives include, but are not limited to, 40-O-(2-hydroxy) ethyl-rapamycin (trade name everolimus from Novartis), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus, manufactured by Abbott Labs.), AP23572 (Ariad Pharmaceuticals), prodrugs thereof, co-drugs thereof, and combinations thereof.

An anti-inflammatory drug can be a steroidal anti-inflammatory drug, a nonsteroidal anti-inflammatory drug (NSAID), or a combination thereof. Examples of anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. Alternatively, the anti-inflammatory agent can be a biological inhibitor of pro-inflammatory signaling molecules. Anti-inflammatory biological agents include antibodies to such biological inflammatory signaling molecules. In addition, the bioactive agents can be other than antiproliferative or anti-inflammatory agents. The bioactive agents can be any agent that is a therapeutic, prophylactic or diagnostic agent. In some embodiments, such agents can be used in combination with antiproliferative or anti-inflammatory agents. These bioactive agents can also have antiproliferative and/or anti-inflammmatory properties or can have other properties such as antineoplastic, antimitotic, cystostatic, antiplatelet, anticoagulant, antifibrin, antithrombin, antibiotic, antiallergic, and/or antioxidant properties. Examples of antineoplastics and/or antimitotics include, but are not limited to, paclitaxel (e.g., TAXOL® available from Bristol-Myers Squibb), docetaxel (e.g., Taxotere® from Aventis), methotrexate, azathioprine, vincristine, vinblastine, fluorouracil, doxorubicin hydrochloride (e.g., Adriamycin® from Pfizer), and mitomycin (e.g., Mutamycin® from Bristol-Myers Squibb). Examples of antiplatelet, anticoagulant, antifibrin, and antithrombin agents that can also have cytostatic or antiproliferative properties include, but are not limited to, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as ANGIOMAX (from Biogen), calcium channel blockers (e.g., nifedipine), colchicine, fibroblast growth factor (FGF) antagonists, fish oil (e.g., omega 3-fatty acid), histamine antagonists, lovastatin (a cholesterol-lowering drug that inhibits HMG-CoA reductase, brand name Mevacor® from Merck), monoclonal antibodies (e.g., those specific for platelet-derived growth factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetics, 4-amino-2,2,6,6-tetramethylpiperidine-1-oxyl (4-amino-TEMPO), estradiol, anticancer agents, dietary supplements such as various vitamins, and a combination thereof. Examples of cytostatic substances include, but are not limited to, angiopeptin, angiotensin converting enzyme inhibitors such as captopril (e.g., Capoten® and Capozide® from Bristol-Myers Squibb), cilazapril and lisinopril (e.g., Prinivil® and Prinzide® from Merck). Examples of antiallergic agents include, but are not limited to, permirolast potassium. Examples of antioxidant substances include, but are not limited to, 4-amino-2,2,6,6-tetramethylpiperidine-1-oxyl (4-amino-TEMPO). Other bioactive agents include anti-infectives such as antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary vasodilators; peripheral and cerebral vasodilators; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents. Other biologically active agents that can be used include alpha-interferon, genetically engineered epithelial cells, tacrolimus and dexamethasone.

A "prohealing" drug or agent, in the context of a blood-contacting implantable device, refers to a drug or agent that has the property that it promotes or enhances re-endothelialization of the arterial lumen to promote healing of the vascular tissue. The portion(s) of an implantable device (e.g., a stent) containing a prohealing drug or agent can attract, bind and eventually become encapsulated by endothelial cells (e.g., endothelial progenitor cells). The attraction, binding, and encapsulation of the cells will reduce or prevent the formation of emboli or thrombi due to the loss of the mechanical properties that could occur if the stent was insufficiently encapsulated. The enhanced re-endothelialization can promote the endothelialization at a rate faster than the loss of mechanical properties of the stent. "Endothelial progenitor cells" refer to primitive cells made in the bone marrow that can enter the bloodstream and go to areas of blood vessel injury to help repair the damage. Endothelial progenitor cells circulate in adult human peripheral blood and are mobilized from bone marrow by cytokines, growth factors, and ischemic conditions. Vascular injury is repaired by both angiogenesis and vasculogenesis mechanisms. Circulating endothelial progenitor cells contribute to repair of injured blood vessels mainly via a vasculogenesis mechanism. In some embodiments, the prohealing drug or agent can be an endothelial cell (EDC)-binding agent. In certain embodiments, the EDC-binding agent can be a protein, peptide or antibody, which can be, e.g., one of collagen type 1, a 23 peptide fragment known as single chain Fv fragment (scFv A5), a junction membrane protein vascular endothelial (VE)-cadherin, and combinations thereof. Collagen type 1, when bound to osteopontin, has been shown to promote adhesion of endothelial cells and modulate their viability by the down regulation of apoptotic pathways. S. M. Martin, et al., *J. Biomed. Mater. Res.*, 70A:10-19 (2004). Endothelial cells can be selectively targeted (for the targeted delivery of immunoliposomes) using scFv A5. T. Volkel, et al., *Biochimica et Biophysica Acta,* 1663:158-166 (2004). Junction membrane protein vascular endothelial (VE)-cadherin has been shown to bind to endothelial cells and down regulate apoptosis of the endothelial cells. R. Spagnuolo, et al., *Blood,* 103:3005-3012 (2004). In a particular embodiment, the EDC-binding agent can be the active fragment of osteopontin, (Asp-Val-Asp-Val-Pro-Asp-Gly-Asp-Ser-Leu-Ala-Try-Gly). Other EDC-binding agents include, but are not limited to, EPC (epithelial cell) antibodies, RGD peptide sequences, RGD mimetics, and combinations thereof. In further embodiments, the prohealing drug or agent can be a substance or agent that attracts and binds endothelial progenitor cells. Representative substances or agents that attract and bind endothelial progenitor cells include antibodies such as CD-34, CD-133 and vegf type 2 receptor. An agent that attracts and binds endothelial progenitor cells can include a polymer having nitric oxide donor groups.

The foregoing biologically active agents are listed by way of example and are not meant to be limiting. Other biologically active agents that are currently available or that may be developed in the future are equally applicable.

In a more specific embodiment, optionally in combination with one or more other embodiments described herein, the implantable device of the invention comprises at least one biologically active agent selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, dexamethasone acetate, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), AP23572 (Ariad Pharmaceuticals), pimecrolimus, imatinib mesylate, midostaurin, clobetasol, progenitor cell-capturing antibodies, prohealing drugs, prodrugs thereof, co-drugs thereof, and a combination thereof. In a particular embodiment, the bioactive agent is everolimus. In another specific embodiment, the bioactive agent is dexamethasone acetate.

While particular embodiments of the present invention have been shown and described, it will be obvious to those skilled in the art that changes and modifications can be made without departing from this invention in its broader aspects. Additionally, all embodiments of the invention can be used or performed in combination with each other. Therefore, the claims are to encompass within their scope all such changes and modifications as fall within the true spirit and scope of this invention.

What is claimed is:

1. A method of manufacturing a stent having a coating, comprising:
    (a) providing a tubular stent having a lumenal side and an ablumenal side;
    (b) applying a coating composition to the stent such that the coating composition contacts the lumenal and ablumenal sides of the stent; and
    (c) modifying the diameter of the stent from a first diameter to a second diameter during the applying of the coating composition, wherein the modifying includes changing the position of a frame element of the stent relative to another frame element of the stent.

2. The method of claim 1, wherein the modification causes the thickness of the coating manufactured on the ablumenal side of the stent to be 25% to 300% greater than the thickness of coating manufactured on the lumenal side of the stent.

3. The method of claim 1, wherein the modification causes the thickness of the coating manufactured on the ablumenal side of the stent to be less than the thickness of coating manufactured on the lumenal side of the stent.

4. The method of claim 1, additionally comprising applying a second coating composition to the stent such that the second coating composition is applied only subsequent to or only during the modification of the first diameter to the second diameter.

5. The method of claim 4, wherein the first and second coating compositions includes one or more polymer(s) and drug(s) with the proviso that any one of the constituents for the first or second composition can be the same or different in type, property, composition, or amount.

6. The method of claim 1, wherein the modifying comprises reducing the diameter of the stent.

7. The method of claim 6, wherein the modifying comprises reducing the diameter of the stent by 3% to 97%.

8. The method of claim 6, wherein the modifying comprises reducing the diameter of the stent from a range selected from the group consisting of 10% to 90%, 20% to 80%, 30% to 70% and 40% to 60%.

9. The method of claim 1, wherein the modifying comprises increasing the diameter of the stent.

10. The method of claim 9, wherein the modifying comprises increasing the diameter of the stent by 3% to 97%.

11. The method of claim 9, wherein the modifying comprises increasing the diameter of the stent from a range selected from the group consisting of 10% to 90%, 20% to 80%, 30% to 70% and 40% to 60%.

12. The method of claim 1, wherein the modification of the diameter of the stent is after the application of the coating composition, wherein the application of the coating composition is completely terminated while the diameter of the stent is modified, and wherein the application of the coating composition is then resumed again after the modification of the diameter of the stent.

13. The method of claim 1, wherein the coating composition is continuously applied while the diameter of the stent is modified such that application of the composition is not disrupted.

14. The method of claim 1, wherein application of the coating composition is by a spray technique and wherein the spray is continuously applied while the diameter of the stent is modified such that application of the composition is not disrupted.

15. The method of claim 1, wherein application of the coating composition is by a spray technique and wherein stent is rotated about a longitudinal axis of the stent.

16. A method of manufacturing a stent having a coating, comprising:
   (a) applying a coating composition to the stent positioned at a first diameter on a stent support structure such that the coating composition contacts the lumenal and ablumenal sides of the stent;
   (b) modifying the diameter of the stent from the first diameter to a second diameter, the modifying including changing the position of a frame element of the stent relative to another frame element of the stent; and
   (c) applying a second coating composition to the stent having the second diameter to manufacture a stent coating.

17. The method of claim 16, wherein the modification comprises decreasing the diameter of the stent such that an ablumenal side of the stent receives a greater amount of the second coating composition than the lumenal side of the stent.

18. The method of claim 16, wherein the modification comprises increasing the diameter of the stent.

19. The method of claim 16, wherein acts (a), (b) and (c) of claim 16 are done in sequential order, such that each of (a), (b) and (c) is fully terminated or discontinued prior to the start of the next act.

20. The method of claim 16, wherein acts:
   (i) (a), (b) and (c) are performed continuously without any disruption in application of the first coating composition and modification of the diameter of the stent and the modification of the diameter of the stent and the application of the second coating composition;
   (ii) (a) and (b) of claim 16 at least in part overlap, followed by termination of act (a) and/or (b), followed by act (c); or
   (iii) (a) is performed, then terminated, followed by (b) and (c) at least in part overlapping.

21. The method of claim 16, wherein the diameter of the stent is modified during a period of application of the first and/or second coating compositions.

22. The method of claim 16, wherein the diameter the stent is held constant during at least a period of application of the first and/or second coating compositions.

23. The method of claim 16, wherein the first composition comprises a polymer and a solvent to form a primer and the second composition comprises a polymer, a solvent and a drug to form a drug layer.

24. The method of claim 16, wherein the first composition comprises a polymer, a drug and a solvent the second composition comprises a polymer, a solvent and optionally a drug.

25. The method of claim 1, wherein the changing of the position of the frame element includes positioning the frame elements closer to one another in order to decrease the diameter of the stent.

26. The method of claim 1, wherein the changing of the position of the frame element includes positioning the frame elements wider apart from one another in order to increase the diameter of the stent.

27. The method of claim 16, wherein the changing of the position of the frame element includes positioning the frame elements closer to one another in order to decrease the diameter of the stent.

28. The method of claim 16, wherein the changing of the position of the frame element includes positioning the frame elements wider apart from one another in order to increase the diameter of the stent.

* * * * *